United States Patent
Qi et al.

(10) Patent No.: US 6,893,642 B1
(45) Date of Patent: May 17, 2005

(54) ALGAE PROTEIN POLYSACCHARIDE EXTRACTION AND USE THEREOF

(76) Inventors: Qing Qi, 451, Beijing Office of Seven-province, Haidian District, Beijing 100088 (CN); Jian Ding, Room 1005, No. 10, Keyuan New Village, Guanshengyuan Road, Shanghai 200233 (CN)

(*) Notice: Subject to any disclaimer, the term of this patent is extended or adjusted under 35 U.S.C. 154(b) by 74 days.

(21) Appl. No.: 10/031,520

(22) PCT Filed: Jul. 19, 2000

(86) PCT No.: PCT/CN00/00205

§ 371 (c)(1),
(2), (4) Date: Jan. 17, 2002

(87) PCT Pub. No.: WO01/05414

PCT Pub. Date: Jan. 25, 2001

(30) Foreign Application Priority Data

Jul. 19, 1999 (CN) ........................................ 99109881 A

(51) Int. Cl.$^7$ ................................................. A61K 35/80
(52) U.S. Cl. .................... 424/195.17; 514/54; 435/101; 435/71.2; 435/71.1; 435/257.1; 435/946
(58) Field of Search ...................... 514/54; 424/195.17; 435/101, 71.2, 71.1, 257.1, 946

(56) References Cited

U.S. PATENT DOCUMENTS 5,585,365 A * 12/1996 Hayashi et al. ............... 514/54

FOREIGN PATENT DOCUMENTS

| CN | 94109295 | 3/1996 |
| CN | 95110950.2 | 9/1996 |
| JP | 58-128322 | * 7/1983 |

OTHER PUBLICATIONS

The Use Spirulina in the Cosmetics, vol. 7, No. 2, Oct., 1998, Journal of Yunan Institute of the Nationalities, Xiaolong Zhu and Hong Li.

Effects of Phycocyanin from Spirulina Platensis on Immune Function in Mice, vol. 19, No. 5, Oct. 1998, Journal of Jinan University, Mei Tang, Ying Jin, Baojiang Guo and Changren Zhou.

* cited by examiner

Primary Examiner—Francisco Prats
(74) Attorney, Agent, or Firm—Volpe and Koenig, P.C.

(57) ABSTRACT

The present invention provides a pharmaceutical composition containing proteoglycan extracts of algae and a process for preparing proteoglycan extracts from the algae.

54 Claims, 4 Drawing Sheets

ALGAE PROTEIN POLYSACCHARIDE EXTRACTION AND USE THEREOF

FIELD OF THE INVENTION

The present invention relates to an extract from algal organisms and its uses, especially to a proteoglycan extract of algae and uses thereof.

TECHNICAL BACKGROUND OF THE INVENTION

Since 70's, researchers have paid much more attention to studies on algal organisms, especially on blue-green algae. These studies are mainly concentrated on nutritional values and toxicity of the organisms. Of these, spirulina has been considered to be an excellent food resource of human in the future as early as in the Food and Agricultural Organization of the United Nations Conference held in 1974.

The properties of various extracts of algal organisms have been studied since 80's to see whether extracts of algal organisms can be used as potential pharmaceuticals. Of the studies, extracts of blue-green algae, in particular extracts of spirulina have been considered great significance.

Japanese patent application 58-128322 discloses a proteoglycan extracted from microalgae and spirulina inhibiting the growth of leukemia cells. However, no other activities of such a proteoglycan have been disclosed in this application. Although a process for extraction of the proteoglycan from spirulina disclosed therein, the process fails to involve the step of breaking the cellular wall of spirulina. Therefore, the process in this Japanese patent application is expected to be only applied in the laboratory, rather than in the industry with a large scale.

This invention is brought forward based on the inventors' studies on the extraction of proteoglycan of algae and therapeutic activities of the proteoglycan extract of algae.

SUMMARY OF THE INVENTION

One object of the present invention is to provide an anticancer composition comprising a therapeutically effective amount of proteoglycan extracts of algae and/or a pharmaceutically acceptable carrier.

Another object of the present invention is to provide a hemogram-improving composition comprising a therapeutically effective amount of proteoglycan extracts of algae and/or a pharmaceutically acceptable carrier.

Another object of the present invention is to provide an anti-irradiation composition comprising a therapeutically effective amount of proteoglycan extracts of algae and/or a pharmaceutically acceptable carrier.

Another object of the present invention is to provide a DNA-repairing composition comprising a therapeutically effective amount of proteoglycan extracts of algae and/or a pharmaceutically acceptable carrier.

Another object of the invention is to provide an antivirus composition comprising a therapeutically effective amount of proteoglycan extracts of algae and/or a pharmaceutically acceptable carrier.

Another object of the invention is to provide an immunoenhancing composition comprising a therapeutically effective amount of proteoglycan extracts of algae and/or a pharmaceutically acceptable carrier.

Further another object of the invention is to provide a dedrite-like-cell-activating composition comprising a therapeutically effective amount of proteoglycan extracts of algae and/or a pharmaceutically acceptable carrier.

Still another object of the invention is to provide a process for preparing a proteoglycan extract of algae, including the following steps of:

a. dissolving dry powder of blue-green algae in 5–20 times water by weight, and conducting cellular walls-breaking;

b. heating a solution obtained from step a) at 60°–100° C., and cooling to separate a liquid phase from the solution;

c. adjusting pH of the liquid phase to less than 7, and filtering; and d. adjusting the filter to pH 7, concentrating, and drying if necessary.

DETAILED DESCRIPTION OF THE INVENTION

Figure 1:
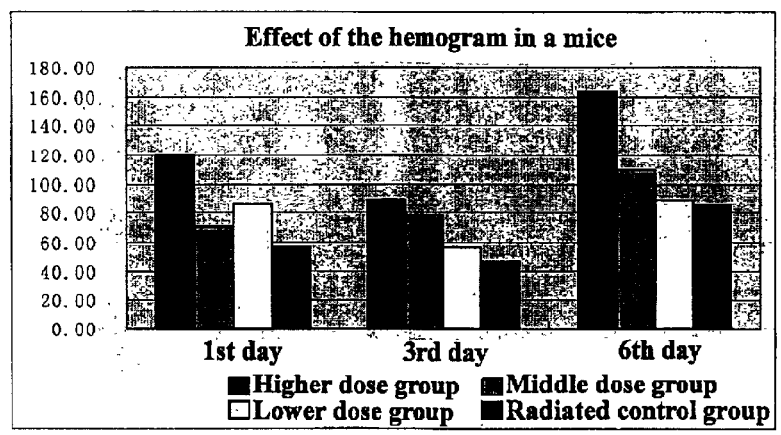
FIG. 1 shows the effect of the hemogram in mice of a hemogram-improving composition of this invention.

This invention provides a pharmaceutical composition comprising a proteoglycan extract of algae and/or a pharmaceutically acceptable carrier. In the composition of the invention, the amount of the proteoglycan extract of algae used is therapeutically effective. Since algal organisms have no by-effect on human being, the proteoglycan extract of algae used in the invention does in general not need to further be purified. However, the extract can be further processed to get a product of a higher purity, if necessary.

The amount of proteoglycan extract of algae used in the invention, which is generally named with the term "therapeutically effective amount" in this application, can readily be determined by those skilled in the art. It depends on the circumstances of a patient, such as body weight, age, disease condition of the patient and the like. As stated before, the proteoglycan extract of algae used in the invention has no by-effect, it may directly be administered to patients. In this case, the composition comprises no pharmaceutically acceptable carriers. In case the composition contains a pharmaceutically acceptable carrier, the extract and the carrier can be mixed according to a conventional process in this field to obtain a desired preparation. Generally, the amount of the active component in the composition may be 0.1%–99.9% by weight.

Pharmaceutically acceptable carriers used in the invention include those conventionally used in the art, such as solvents, excipients and disintegrating agents. Pharmaceutical composition may be prepared as any conventional forms including oral solutions, capsules, troches, pills, powders, granules, syrups, suppositories, etc.

Powders of algae are preferably used as raw materials in the invention for extracting proteoglycan of algae. Cellular wall-breaking in step a) may be conducted in any conventional manners in the art, such as a supersonic treatment, a quickly stirring, an osmotic-pressure-changing lysis, or an enzymolysis.

To remove the cultures and impurities on the surface of algal powders, the surface of the powders may firstly be washed with little water. Generally, the time for heating in step b) of the invention is from 0.5 h to 2 h, preferably 1 h, and the temperature therefor is in the range of 60° C.–100° C., preferably 80° C.–95° C., and more preferably at 95° C.

The amount of water used in the process of invention may be as 8–15 times by weight as that of algal powders used, preferably as 10 times by weight.

In step c), the solution is first adjusted to pH<7, preferably to pH 2.0–4.5, and more preferably to pH 3.8–4.2. Conventional acids/bases such as a HCl or $H_2SO_4$ solution and a $Na_2CO_3$ or $NaHCO_3$ solution, may be used to adjust the pH value in this step.

In this invention, methods for separation between a solid phase and a liquid phase are those conventionally used in the art, such as filtration under a reduced pressure, molecular sieve filtration, centrifugation and the like. Because of the treatment of breaking cellular walls involved in this invention, proteoglycan extracts of algae may be obtained in a higher yield.

Proteoglycan extracts of algae obtained by the process of the invention have activities of anticancer, anti-irradiation, immunoenhancing, DNA-repairing, dendrite-like-cell-activating, hemopoietic function-improving and the like.

This invention will further be described with the following examples.

PREPARATION OF PROTEOGLYCAN EXTRACTS OF ALGAE

EXAMPLE 1

3 kg of Spirulina powder was dissolved in 3 L of water, and then filtered. To a solution was added 30 L water and stirred rapidly. Resultant solution was heated at 88° C. for 1 h. After cooling, the solution was filtered under a pressure. Then, the filtrate was adjusted to pH 3.8 with a dilute solution of HCl and kept overnight. After centrifugation, the supernatant was adjusted to pH 7 with a solution of $Na_2CO_3$. Resultant precipitates were spry-dried to obtain a crude extract of spirulina 0.599 kg, which contains 72.3% of proteoglycan.

EXAMPLE 2

3 kg of Spirulina powder was dissolved in 24 L of water, stirred and heated at 90° C. for 1 h. After cooling, the resultant was filtered under a reduced pressure. The filtrate was adjusted pH 4.2 with HCl and kept overnight. After filtration, the filtrate was adjusted to pH 7 with a solution of $NaHCO_3$. Resultant precipitates were dried to obtain a crude proteoglycan extract of Spirulina 0.549 kg, containing 71.2% of proteoglycan.

Biological Assays

1. Anti-irradiation Activity

150 C-57 mice (18–22 g) purchased from the Animal Center of Chinese University of Medical Sciences were used. Of them, 120 mice were irradiated with $^{60}Co$-γ, at 600 rad, 8.64 rad/min.

The irradiated mice were randomly divided into a control group, a lower dose group, a middle dose group, and a higher dose group, each with 30 mice, while 30 not-irridiated mice were used as a blank control group. Mice in the lower, middle, higher dose groups were administrated with the proteoglycan extract of spirulina obtained in Example 1 at a dose of 10 mg/kg/d, 20 mg/kg/d, 40 mg/kg/d, respectively, whereas mice in the blank and control groups were not administrated with the extract. In ten days, survival rate of the mice in each group was shown in the following table.

| Groups | Days after irradiation | | | | Survival rate (%) in 10 days |
|---|---|---|---|---|---|
| | 0 | 3 | 6 | 10 | |
| Higher Dose | 30 | 30 | 26 | 22 | 73 |
| Middle Dose | 30 | 30 | 26 | 19 | 63 |
| Lower Dose | 30 | 30 | 26 | 10 | 33 |
| Control | 30 | 6 | 6 | 3 | 10 |
| Blank | 30 | 30 | 30 | 30 | 100 |

The result showed that survival rate of the mice in the administrated group was significantly higher than in the control group, proving that proteoglycan extract of spirulina possesses potent anti-irradiation activity, especially at a middle or higher dose.

2. Improving Hemopoietic Function and Hemogram and Enhancing the Number of Blood Platelet Experiment 1

Hemogram Examination

C-57 mice (18–22 g) purchased from the Animal Center of the Chinese University of Medical Sciences were used. One hundred and twenty mice were irradiated with $^{60}Co$-γ, at 600 rad, 8.64 rad/min.

The irradiated mice were randomly divided into a control group, a positive control group, a lower dose group, a middle dose group, and a higher dose group, while 30 not-irradiated mice were used as a blank group. Mice in the positive group were administrated with shengxuewan (Tianjin Darentang Pharmaceutical Factory, China) at 6000 mg/kg/d (as 20 times as an adult usually administrated). Mice in the lower, middle and higher dose groups were administrated with a proteoglycan extract of spirulina obtained in Example 1 at 10 mg/kg/d, 20 mg/kg/d, 40 mg/kg/d, respectively, whereas mice in the blank and control groups were not administrated with the extract. Blood samples were taken from the tail vein of mice on the first day, the third day, the sixth day, respectively, after irradiation, and examined by a conventional hemogram-examining method.

The results were shown as follows:

| Groups | Days after irradiation | | |
|---|---|---|---|
| | First day (n = 10) | Third day (n = 10) | Sixth day (n = 7) |
| Higher dose group | 120 ± 10.62 (<0.01) | 89.3 ± 3.59 (<0.01) | 163.7 ± 22.1 (<0.01) |
| Middle dose group | 70.6 ± 7.74 (<0.3) | 78.2 ± 13.3 (<0.05) | 109.3 ± 8.03 (<0.02) |
| Lower dose group | 86.1 ± 9.79 (<0.05) | 56.7 ± 4.34 (<0.3) | 89.0 ± 9.76 (>0.5) |
| Irradiation control Group | 57.2 ± 6.02 | 47.0 ± 3.82 | 85.6 ± 4.5 |
| Blank control Group | 354.4 ± 25.2 | 277.1 ± 28.12 | 313.3 ± 24054 |

The data in table were expressed as WBC±SE and the total leukocyte number equals fifty times of the counting number while the data in brackets were P values compared with the irradiation control group and n is the animal number in each group.

The experiment showed that the number of leukocyte in treated groups is higher than that in the irradiation control group, particularly in the higher dose group (P<0.01). As seen in FIG. 1, even the effect in the lower dose group also exceeded the control group.

Experiment 2

One naval department processed a project under strong radiant conditions to make participants suffering radiant damage in the different degrees. After proteoglycan extracts of spirulina according to the invention were administrated, the number of leukocytes of the patients was increased, and the immunity thereof was enhanced. It showed that proteoglycan extracts of spirulina of the invention had effects on increasing leukocytes.

Experiment 3

30 persons whose level of leukocytes and platelets was relatively lower than that of the normal were tested. The proteoglycan extract of spirulina was orally administrated to the patients, twice a day and three tablets each time. After one month, 73 percent of the patients significantly increased in leukocytes and platelets, and the condition of the diet, rest and mental were improved. There was little effect on the other 26 percent of the patients since the number of their original leukocytes was not lower and still kept in the normal range.

Experiment 4
Platelets Counting Assay

According to the requirements of the guidelines of novel drug on pre-clinical research, issued by the Chinese government, therapeutic effect of the proteoglycan extract of spirulina on beagle dogs was observed. The dogs were radiated with 6.5Gy$^{60}$Co-γ unevenly. The dogs were then administrated with an oral liquid for increasing leukocytes, produced by Zhengzhou Pharmaceutic Co. Ltd, as a positive control group. The dogs were administrated with capsules (360 mg) made from the proteoglycan extracts according the invention as treated groups, three days before irradiation, and consecutively for 24 days. Results showed that there was little change to the specific volumes of leukocytes, granular leucocytes, red blood cells, haematoglobin and the blood cells of peripheral blood for the dogs in the positive control group. However, the amount of platelets for the dogs in each treated groups was obviously higher than that of the control group at the second and fourth week after irradiation (P<0.01). Furthermore, the recovery of the medullary macronucleocytes was also accelerated as well as the increase of the amount of macronucleocytes in marrow slides of the dogs in the treated groups. The transforming rate of the peripheral blood lymphocytes of the dogs in treated groups was also higher that that of an irradiation control (a blank control) group and the positive control group.

The above results showed that the proteoglycan extract of the invention can obviously recover the amount of the peripheral blood platelets and the transforming rate of the lymphocytes of beagle dogs after irradiation, and promote the proliferation of hematoblasts of the medullary macronuclear system thereof. Therefore, it is expected as a therapeutic agent to treat the tumor patients in radiotherapy and chemotherapy in a higher dose or the acute irradialized patients lacking the platelets or having decreased immune function.

3. Growth Inhibition of Various Tumor Cell Lines

The proteoglycan extract according to the invention had distinct inhibitory effects on the proliferation of human leukemia cell lines such as U937, HL60 and P388 as well as human lung cancer A549, human hepatocellular hepatoma HepG2 and human gastric adenocarcinoma MKN-28, HCT116 in vitro. And it also exerted obvious inhibition from the growth of mouse S180 sarcoma, B16 melanoma and human gastric adenocarcinoma MKN-28, SGC-7901 and human lung adenocarcinoma LAX83 nude mice xenografts in vivo.

Expreiment 1
Growth Inhibition of Various Tumors In Vitro
Tumor cell lines tested:
  P388: mouse lymphoma
  U937: human monocyte leukemia
  HL60: human myeloid leukemia
  K562: human erythroleukemia
  A-549: human non-small cell lung cancer
  SPC-A4: human lung adenocarcinoma
  DMS-114: human small cell lung cancer
  NCI-H23: human lung adenocarcinoma
  SGC-7901: human gastric middle-differentiated adenocarcinoma
  MKN-28: human gastric high-differentiated adenocarcinoma
  HCT-116: human colon low-differentiated adenocarcinoma
  Hep-G2: human hepatocellular hepatoma
  MCF-7: human breast cancer
  A-431: human dermal squamous cancer
The above cell lines are all kept and cultured in our lab.
Measurements Suspended tumor cell lines, P-388, U-937, HL-60 and K-562 were measured by microculture tetrazolium (MTT) assay. Tumor cells in 90 μl medium were seeded into each well of 96-well microculture plates at appropriate densities to maintain the cells in an exponential stage of growth during the experiment. Then, a solution of the proteoglycan extract obtained in the invention was added to each well, 10 μl/well. According to the pre-assay results, the proteoglycan extract of spirulina was designed for five concentrations and each was tested in triplicate wells. The blank having no cells and DMSO controls should be set for. After incubation at 37° C., 5% $CO_2$ for 48 h, 20 μl of 5 mg/ml MTT solution was added to each well. After a further incubation was taken for 4 h at 37° C., 50 μl of a triplex solution (10% SDS-5% isobutanol-0.01 mol/L HCl) was added to each well and the plates were incubated overnight under $CO_2$. The optical density (OD) was read on a plate reader at a wavelength of 570 nm. The inhibitory rate of the cell proliferation was calculated by the following formula and the $IC_{50}$ value was calculated by the Logit method.

Other cell lines were measured by the Sulforhodamine B (SRB) assay. The adherent tumor cells were firstly allowed to attach for 24 h then cultured by the same method as MTT assay. Briefly, after the attachment for 24 h, the proteoglycan extract of spirulina at different concentrations was added to the well and the plates were cultured at 37° C. for 72 h. The mediums were removed and the cell were fixed by 100 μl of 10% cold solution of trichloroacetic acid to each well, followed by incubation at 4° C. for 1 h. The plates were washed with de-ionized water five times and dried in the air. The cells were then stained by 100 μl of SRB (Sigma) solution in 1% acetic acid (V/V) per well for 15 min. After stained, the supernatant was removed and the plates were quickly washed five times with 1% acetic acid to remove the unbound dye and allowed to air dry. Bound dye was solubilized with 150 μl of 10 mmol/L Tris base each well, then the optical density (OD) was read on a plate reader at a wavelength of 570 nm. The inhibitory rate and the IC50 value was calculated by the same method as the MTT assay.

Growth Inhibitory Rate(%)=(ODcontrol−ODtreated)×100%/ODcontrol

TABLE I

Inhibition rates (%) and IC50 values of the proteoglycan extract of spirulina on proliferation of tumor cell lines in vitro Conc. (mg/ml)

| Cell lines (mg/ml) | 5 | 1.67 | 0.56 | 0.185 | 0.062 | IC50 |
|---|---|---|---|---|---|---|
| P-388 | 90.7 | 72.1 | 31.4 | 5.8 | 1.2 | 1.03 |
| HL-60 | 95.7 | 63.8 | 25.5 | 17.0 | 0.0 | 1.22 |
| U-937 | 87.5 | 66.1 | 35.7 | 37.5 | 3.6 | 0.93 |
| MKN-28 | 76.2 | 55.4 | 24.8 | 20.8 | 14.9 | 1.29 |
| SGC-7901 | 48.3 | 6.2 | 2.1 | 3.4 | 0.0 | — |
| A-431 | 0.0 | 0.0 | 0.0 | 1.8 | 4.6 | — |
| SPC-4 | 41.2 | 23.5 | 26.5 | 9.8 | 0.0 | — |
|  | 5 | 3.3 | 2.2 | 1.48 | 0.99 |  |
| A-549 | 92.4 | 86.4 | 50.0 | 30.3 | 54.5 | 2.00 |
| NCI-H23 | 30.9 | 10.3 | 0.0 | 4.4 | 0.0 | — |
| DMS-114 | 75.0 | 63.5 | 46.2 | 36.5 | 19.2 | 2.36 |
| Hep-G2 | 85.9 | 87.5 | 75.0 | 39.8 | 23.4 | 1.61 |
| K562 | 85.1 | 73.1 | 41.8 | 29.9 | 19.4 | 2.18 |
| MCF-7 | 0.0 | 6.3 | 20.8 | 1.7 | 0.0 | — |
| HCT-116 | 86.1 | 65.7 | 44.4 | 30.6 | 24.1 | 2.15 |

Experiment 2
Inhibitory Effect on DNA-topoisomerase and Direct Influence on DNA of Proteoglycan Extracts of Spirulina DNA topological structures of eukaryotic organisms are regulated by two classes of key enzymes, topoisomerase I (Topo I) and topoisomerase II (Topo II). Topo I can give rise to the break-up of a single-stranded DNA and plays an important role in DNA replication, transcription and chromosome organization although it isn't necessary for the survival of an eukaryotic cell. Topo II is necessary for a cell and can catalyze the break-up of a double-stranded DNA and plays an important role in DNA replication, transcription, recombination as well as forming the accurate chromosomal structure, chromosome segregation and condensation. In virtue of their critical functions and catalytic characterization, Topo I and Topo II have been identified as extensive targets of chemotherapeutic drugs in clinic.

DNA Topoisomerase inhibitors having DNA intercalation can bind DNA directly, but not break up DNA, while other kind of compounds as "molecular scissors" can cleave DNA directly. Both a DNA Topoisomerase inhibitor and molecular scissors make DNA metabolic turbulence, which gives rise to death of a cell.

Methods:

1. Effect of the proteoglycan extract of spirulina on Topo I activity

The proteoglycan extract of spirulina can inhibit relaxation of Topo I-mediated supercoiled PBR322.

2. Effect of the proteoglycan extract of spirulina on Topo II activity

The proteoglycan extract of spirulina can inhibit decatenation of Topo II-mediated kDNA.

Figure 2:
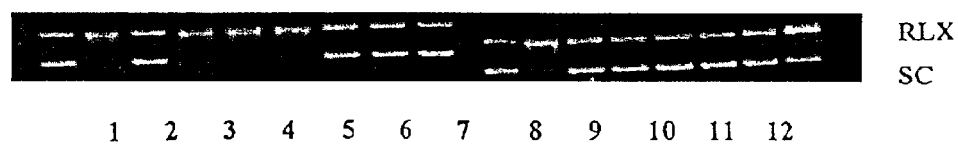
FIG. 2 shows the effect of a proteoglycan extract of algae of this invention inhibiting Topo I-mediated supercoiled DNA relaxation.
Figure 3:
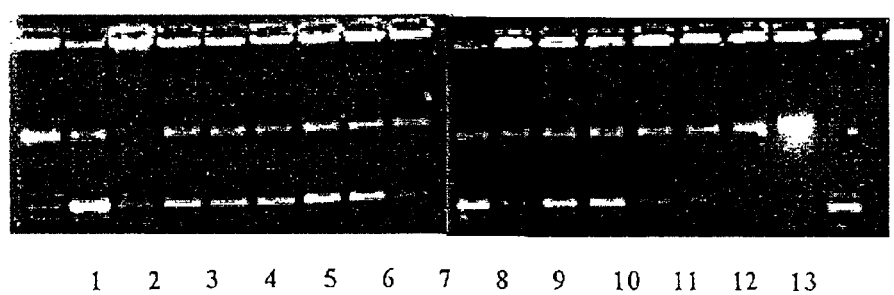
FIG. 3 graphically shows the effect of a proteoglycan extract of algae of this invention inhibiting Topo II-mediated kDNA decatenation

Experimental results were seen in FIGS. 2 and 3.

The proteoglycan extract of spirulina inhibited the Topo I-mediated supercoiled PBR322 relaxation shown in FIG. 2, in which lane 1: PBR322 control; lane 2: 1μ Topo I crude enzyme-extract solution; lane 3: 50 μM OPT; lanes 4–10: 0.64, 3.2, 16, 80, 400, 2000, 10000 μg/ml of DMSO-soluble components of the proteoglycan extract of spirulina; lanes 11–17: 0.64, 3.2, 16, 80, 400, 2000, 10000 μg/ml of water-soluble components of the proteoglycan extract of spirulina.

The proteoglycan extract of spirulina can inhibit the Topo II-mediated kDNA decatenation as shown in FIG. 3, in which:

lane 1: kDNA control; lanes 2 and 10: 1μ Topo II crude enzyme-extract solution; lane 3: 50 mM VP16; lanes 4–9; 0.64, 3.2, 16, 80, 400, 2000 μg/ml of DMSO-soluble components of the proteoglycan extract of spirulina; lanes 11–17: 0.64, 3.2, 16, 80, 400, 2000 μg/ml of water-soluble components of the proteoglycan extract of spirulina; lane 18: 20% DMSO.

The results showed that two kinds of components of the proteoglycan extract of spirulina inhibited Topo I and Topo II activity both in the reaction of Topo I-mediated supercoiled PBR322 relaxation and in the reaction of the Topo II-mediated kDNA decatenation. But there was a relatively obvious difference between them. The water-soluble component had a higher inhibitory effect on Topo I, Topo II and showed a complete inhibitory effect on Topo I activity at 3.2 μg/ml dose, and 16 μg/ml for Topo II activity. The complete inhibitory dose of the DMSO-soluble component was 80 μg/ml for Topo I and 2000 μg/ml for Topo II, respectively.

These experiments indicated that the water-soluble component of the proteoglycan extract of spirulina was main active components inhibiting topoisomerase, whose mechanism might be interacting with DNA firstly, inducing DNA conformation changed, then making the enzyme and substrate contact inefficiently and the enzyme activity decreased, even lost.

In summary, both the components of the proteoglycan extract of spirulina have obvious inhibitory effects on Topo I and Topo II. Furthermore, the water-soluble component can also induce the break-up of a double-stranded DNA directly.

Experiment 3
Effect of the Proteoglycan Extract of Spirulina on Protein Tyrosine Kinase (PTK)

Protein tyrosine kinase (PTK) is a crucial factor in signaling transduction and is associated with the growth, proliferation and transformation of a cell. Many expression products of oncogenes are of PTK's activity, which is much higher in transformed cells than in normal cells. Therefore, it is hypothesized that the unexpected growth of tumor cells may be controlled by decreasing the PTK's activity.

Epidermal growth factor receptor (EGFR), a PTK of receptor type, is a single-stranded trans-membrane glycoprotein consisting of 1186 amino acids, whose molecular weight is 17 kDa, and exists extensively on the epithelial membrane of the mammals. The C end of the EGFR can recognize and activate many cellular substrates after phosphorylated, then effect on metabolization, growth and carcinogenesis of a cell. Numerous researches have been indicated that the EGFR was overexpressed in many tumors and was tightly associated with tumor metastasis and poor prognosis. In our research, we used A431 cell containing the EGFR for picking up PTK, so as to observe the effect of the proteoglycan extract of spirulina on phosphorylation of PTK.

RESULTS

Results 1:

| Conc. (mg/ml) | 5.0 | 2.5 | 1.2 | 0.6 | 0.3 |
|---|---|---|---|---|---|
| Inhibition rate (%) | 100 | 100 | 100 | 67.9 | 65.0 |

Positive control: 2.5 mM tyrphostin 25, inhibition rate: 100%

Results 2:

| Conc. (mg/ml) | 1.5 | 0.75 | 0.4 | 0.2 | 0.1 |
|---|---|---|---|---|---|
| Inhibition rate (%) | 94.1 | 72.5 | 62.7 | 62.7 | 47.1 |

Positive control: 0.25 mM tyrphostin 25, inhibition rate: 86.1%

Results 3:

| Conc. (mg/ml) | 1.2 | 0.6 | 0.3 | 0.15 | 0.07 |
|---|---|---|---|---|---|
| Inhibition rate (%) | 89 | 80.6 | 67.7 | 54.1 | 37.7 |

Positive control: 0.25 mM tyrphostin 25, inhibition rate: 80.5%

The results showed that the proteoglycan extract had a distinct inhibitory effect on the PTK's activity. It almost completely inhibited the tyrosine phosphorylation of PTK at a dose of 1.2 mg/ml and had a 65–67% inhibitory rate at a dose of 0.3 mg/ml, still had a 37.7% inhibitory rate at a lower dose of 0.07 mg/ml.

The above experiments illustrated that the proteoglycan extract of spirulina could distinctly inhibit phosphorylation of the tyrosine residue of PTK. The possible mechanism is that it disrupts PTK-mediated signal transduction by inhibition of the kinase so as to prohibit the malignant growth of tumor cells.

Experiment 4
Proteoglycan Extract of Spirulina Inducing Apoptosis in Human Leukemia HL-60 Cells Apoptosis, regulated by a series of genes, is a programmed cell-death. Its regulatory turbulence was tightly associated with the malignant tumorgenesis. Now it is well-known that many anti-cancer drugs are able to induce apoptosis in tumor cells and the anti-cancer effect is related to the ability of inducing tumor cell apoptosis. Inducing cell apoptosis maybe a common pathway for anti-cancer drugs interfering tumor in different mechanisms, so cell apoptosis becomes one method of evaluating cure efficacy and inducing apoptosis of tumor cells is a target for curing tumor too.

Experiments and Results
Agarose Gel Electrophoresis

Figure 4:
FIG. 4 shows an agarose gel electrophoresis assay of a proteoglycan extract of algae of this invention inducing human HL-60 cell apoptosis.

When cell apoptosis occurred, endonuclease was active, DNA was cleaved between nucleosomes to form DNA fragments about 180–200 bp or those of its multiple. Agarose gel electrohporesis could detect specific DNA ladders, see FIG. 4. In FIG. 4, numeral reference 1 represented a control group, numeral reference 2 represented a proteoglycan extract of spirulina group of 1 mg/ml, numeral reference 3 represented a proteoglycan extract of spirulina group of 3 mg/ml and numeral reference 4 represented a proteoglycan extract of spirulina group of 6 mg/ml.

Flow Cytometry

Figure 5:
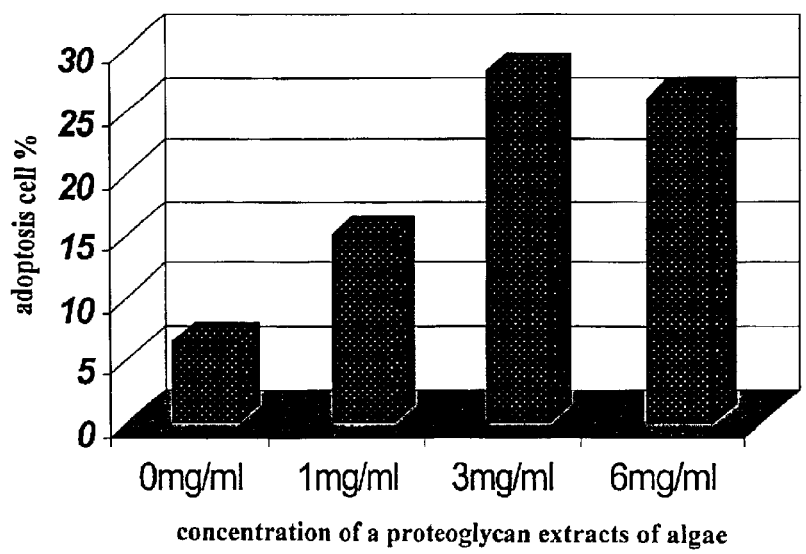
FIG. 5 graphically shows a relationship between a concentration of a proteoglycan extract of algae of this invention and the percentage of apoptosis cell numbers.

When cell apoptosis occurred, disrupt DNA fragments evaded from cells, and the amount of DNA in the cells decreased. Flow cytometry method can detect those cells before G1 phase (also called apoptosis cells), in which the amount of DNA is less than that of diploid cells. Results of the Experiment were shown in FIG. 5.

The experiment demonstrated proteoglycan extracts of Spirulina had inhibit effects on a broad spectrum of human solid tumors and leukemia both in vitro and in vivo. It inhibited the growth of tumor cells as an inhibitory agent of the EGF-R protein tyrosine kinase by blocking signal pathways of proliferation of cells, and also induced a tumor to apoptosis as an inhibitory of topoisomerase by interfering with DNA replication, transcription and gene expression. Proteoglycan extracts of Spirulina had a little toxic, and could clinically be used in a long term. It had significant anti-tumor effects and a clear target to be effected, so it should become a hopeful drug for treating cancers.

4. Repairing DNA
Experiment 1
Bone Marrow Damage Experiment

C-57 mice, body weight of 18–22 g, purchased from Animal Center of the Chinese Medical University. Mice were radiated with a dose of 600 rad $^{60}$Co-γ, 8.64 rad/min.

| Groups | Cells/50 mm$^2$ (Mean) | Percentage of Prematured cells (Mean) | Cell Mitosis |
|---|---|---|---|
| Control group | 140 | 40 | Yes |
| Radiated group | 31 | 4 | None |
| Lower dose group | 72 | 30 | Yes |
| Higher dose group | 74 | 35 | Yes |
| Positive control group | 45 | 35 | Yes |

Mice after radiated were divided into groups of a radiated control, lower dose, middle dose, and higher dose groups. Mice in the control group had not been radiated. Mice in the control group and the radiated control group were treated without drugs, mice in the lower dose group were treated with Proteoglycan extracts of Spirulina at a dose of 10 mg/kg/day, in middle dose group with Proteoglycan extracts of Spirulina at a dose of 20 mg/kg/day, and in the higher dose group with Proteoglycan extracts of Spirulina at a does of 40 mg/kg/day. At the second day after radiation, 10 mice randomly selected from each group were autopsied for tissue slices. Slices were observed under a microscope, amplified with 750 times.

Figure 6:
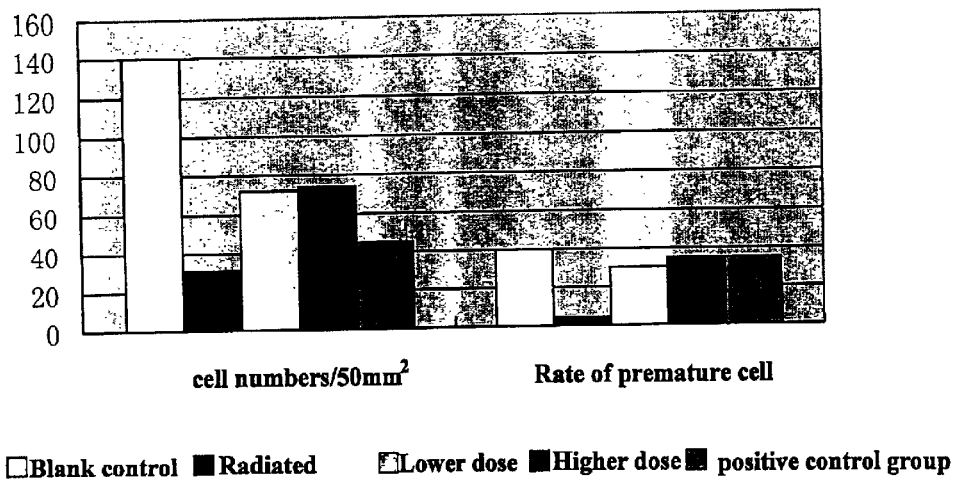
FIG. 6 graphically shows the effect of different compositions according to the invention on a cell of bone marrow in mice.

Experiment results shown in FIG. 6 demonstrated that the damage of radiation to the mice was most significant in the radiated control group. In this group, bone marrow of the mice was of a network-like, cell proliferation thereof was disrupted, premature cell thereof only occupied 4%, and no mitosis was observed. Blood capillary wall in bone marrow was damaged to cause hemorrhage and form a "blood pool". The damage of the mice in the groups treated with drug was reduced.

Experiment 2
Determining the Amount of Bone Marrow DNA

The mice were radiated and treated as above. At the sixth day after radiation, 10 mice randomly selected from each group were autopsied. An intact femur removing all soft tissues was washed with 10 ml solution of 0.005M $CaCl_2$ to introduce all bone marrow into a centrifugal tube, kept at 4° C. for 30 min, and centrifuged with 2500 rpm for 15 min.

Precipitate was fully mixed with 5 ml solution of 0.2 ml/l $HClO_4$, heated at 90° C. for 15 min, and centrifuged after cooling. The value of OD of the supernatant at 286 nm was detected. DNA contents: 1OD=33 µg/ml DNA.

Experimental results were listed as follows:

| Group | Control group | Radiated control group | Lower dose group | Middle dose group | Higher dose group | Positive control group |
|---|---|---|---|---|---|---|
| DNA | 49.04 | 2.01 | 2.71 | 8.94 | 6.34 | 3.56 |
| µg/ml | 27.03 | 2.94 | 8.42 | 10.00 | 4.82 | 2.38 |
|  | 27.92 | 1.58 | 7.19 | 7.79 | 6.14 | 4.79 |
|  | 27.19 |  | 4.42 |  | 3.70 | 6.34 |
| Mean | 32.79 | 2.18 | 5.68 | 8.91 | 5.25 | 4.27 |
| P |  |  | <0.05 | <0.01 | <0.01 | <0.01 |

Figure 7:
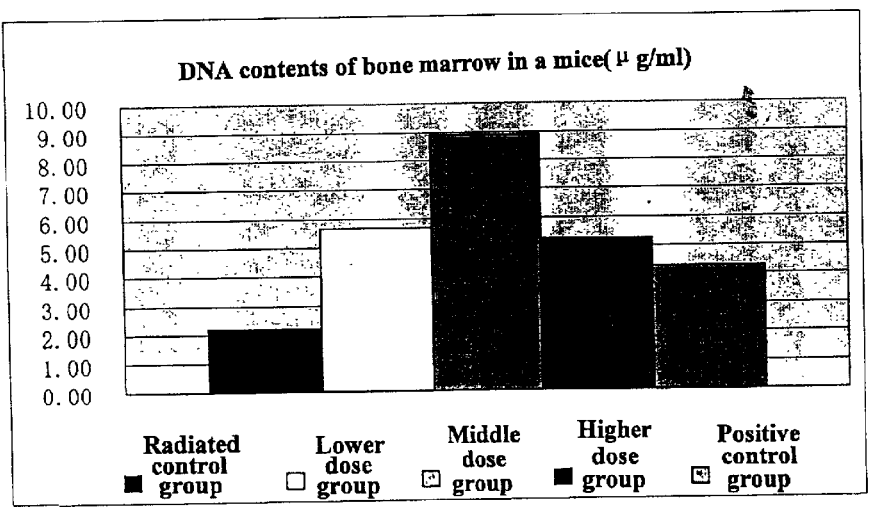
FIG. 7 shows DNA contents of bone marrow in mice under different compositions in accordance with the invention.

The results were also expressed as in FIG. 7, which demonstrated: DNA content in the treated group was higher than that of the radiated control group. The middle dose, higher dose or positive control group, compared to the radiated control group, had a significantly difference (P<0.01). It showed the extract according to the invention protected bone marrow cells, and had obviously repairing effect on DNA.

5. Antiviral Experiment

Clinical pathology:

Patient 1: XXX, male, middle age, a farmer of Daxing County, Beijing. He suffered viral hepatitis, and became cirrhosis later. After 10 year, he had serious ascitic fluid, and hemorrhage in digestive tract. After treated with a capsule made from proteoglycan extracts of Spirulina according to the invention twice daily, 1 capsule per time, there were less ascitic fluid and great hemorrhage after 60 days, there was little ascitic fluid after 90 days, and he could deal with his own daily life, and was recovered. In 1999, he did CT test in hospital, compared with CT result 10 years ago, the focus did not expand or get worse. According to pathologists, it was rare for a patient not to enlarge the focus suffering cirrhosis for 10 years.

Patient 2: XXX, a head of an elementary school in Beijing, had cirrhosis because he did not cure viral hepatitis well, followed with serious ascitic fluid and great hemorrhage in digestive tract and was to die. After treated with proteoglycan extracts of Spirulina, twice daily, one capsule per time, continued 60 days, there were less ascitic fluid obviously, and no great hemorrhage any more. After treated for 90 days, there were little ascitic fluid; after treated with drug for 180 days, he could deal with his own daily life, back to work again, and feel good. In 1999, he did CT test in 301 hospital, and find no focus. Pathologists believed there was evidence to consider that virus was inhibited.

6. Repairing Mucous Membrane Damage

C-57 mice, body weight of 18–22 g, purchased from the Animal Center of Chinese Medical University. Mice were radiated with a dose of 600 rad $^{60}Co$-γ, 8.64 rad/min.

Mice after radiation were divided into groups of a radiated control, a lower dose, middle dose, and a higher dose. Mice in a blank control group were not radiated. Mice in the blank control group and a radiated control group were treated without drugs. Mice in the lower dose group were treated with proteoglycan extracts of Spirulina according to the invention at a dose of 10 mg/kg/day, in the middle dose group at a dose of 20 mg/kg/day, and in the high dose group at a dose of 40 mg/kg/day. At the seventh and fourteenth day after radiation, 10 mice randomly selected from each group were autopsied, and made tissue slices for small intestine. The slices were observed under a microscope, photographed and counted.

Experiment data showed: for the mice in the control group, radiation generated great harm to epithelial cells of small intestine mucous membrane of the mice, caused epithelial cells of mucous membrane of the mince damaged, even disruption. This also made the stratum of the cells naked. However, the harm under radiation to epithelial cells of small intestine mucous membrane of the mice in the treated group was of a significant decrease, compared to the control group.

7. Enhancing Immune System

Experiment 1

Content of γ Globulin

C-57 mice, body weight of 18–22 g, purchased from Animal Center of Chinese Medical University, were radiated with a dose of 600 rad $^{60}Co$-γ, 8.64 rad/min.

Mice after radiation were divided into a radiated control group and a radiated treated group. Mice in a control group and a treated control group were not radiated. Blood harvested from mice's eye sockets was centrifuged and serum was taken therefrom. The serum was conducted a chromatographic analysis after dyeing. The content of γ-globulin in serum was calculated according to peak values.

The results were as follows:

| Group | Mean of γ globulin percentage (±SD) |
|---|---|
| Control | 10.07 ± 3.57 |
| Treated control | 12.84 ± 6.75 |
| Radiated control | 6.19 ± 4.96 |
| Radiated treated | 13.32 ± 6.73 |

Figure 8:
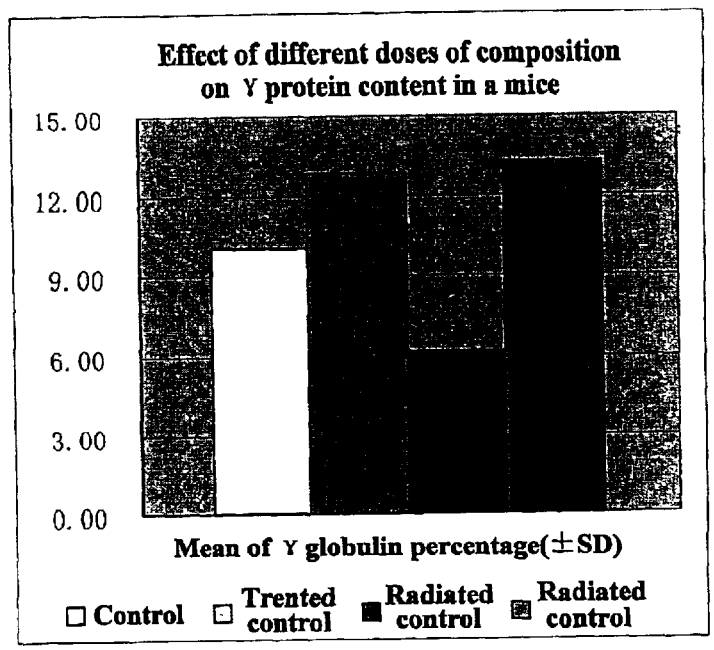
FIG. 8 shows the effect of different doses of compositions according to the invention on τ protein content in mice.

The results are also expressed as in FIG. 8, which demonstrated that the mice both in the radiated group and the not radiated group, γ globulin percentage of the mice in the treated group were higher than that of the corresponding control group. Since the content of γ globulin represents immune function of a body, the increase of γ globulin percentage showed improvement of immune function of a body.

Experiment 2

T-lymphocyte Test

Mice, body weight of 18–22 g, were randomly divided into a blank control group, positive control group, a higher dose group and a lower dose group, with 10 mice per group. The mice in the treated groups were injected with CTX at a dose of 10 mg/kg/d, and then treated with proteoglycan extracts of Spirulina via p.o., at the same dose as above. The mice in the positive control group were treated with CTX at a dose of 10 mg/kg/d, and then treated with water via p.o. the mice in the control group only were treated with water via p.o. after the treatment was continuously taken for 10 days, the treatment was stopped for 2 days. Blood was harvested from eye sockets of the mice for lymphocyte slices. After incubation and dyeing, T-lymphocyte percentage was determined.

Results were shown as follows:

| Groups | T-lymphocyte | P value |
|---|---|---|
| Control | 28.0 ± 2.55 |  |
| Positive control | 25.6 ± 2.51 |  |
| Higher dose | 39.8 ± 7.40 | <0.01 |
| Lower dose | 33.2 ± 6.30 | <0.05 |

Figure 9:
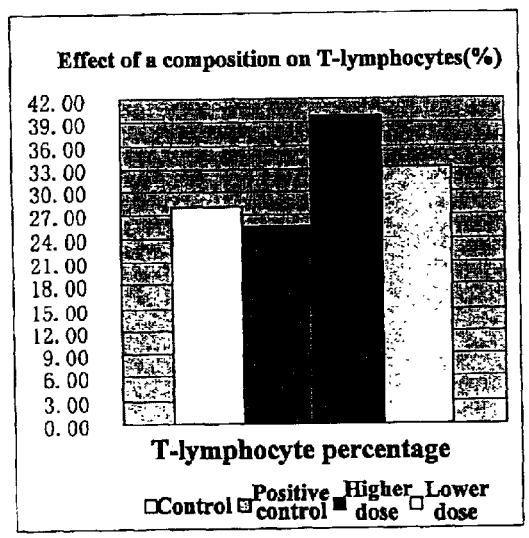
FIG. 9 graphically shows the effect of a composition according to the invention on T lymphocytes.

The results were also expressed as in FIG. 9, which demonstrated that after the mice were injected with CTX, the content of T-lymphocyte of the mice decreased significantly. However, the content of T-lymphocyte of the mice in the treated group increased, especially in the higher dose group, P<0.01. This showed that proteoglycan extracts of Spirulina according to the invention had function of enhancing immune function of a body and protection of bone marrow cells.

8. Proteoglycan Extracts of Spirulina on Proliferation of CD43+ Hemotapoietic Stem/Ancestor Cells Materials and Methods:

All cells were cultured with corresponding cell factors at 37° C. in 15% FCS RPMI 1640 medium under a atmosphere of 5% $CO_2$.

Umbilical core blood CD34+ hemotapoietic stem/ancestor cells

A sample, umbilical core blood came from People Hospital, Department of Gynaecology and Obstetrics, Beijing Medical University. Final concentration of heparin was 20 U/ml. The sample was screened CD34+ cells within 5 hours after harvesting blood. Umbilical core blood was diluted with PBS. Erythrocyte was precipitated with 0.1% methylcellulose, and the supernatant was collected. Monocyte (MNC) was separated with lymphocyte separating medium. Using QBEND-10 as CD34 antibody and sheep anti-mouse IgG1 immune beads (Miltenyi Biotec Co. Germany). Marked cells were passed through separating column in a magnetic field., and un-marked cells is removed by elution. The column was removed from the magnetic field, and eluted under a pressure. CD34+ cells were collected and counted.

Cell Factors

Cell factors and the manufactory thereof in $CD34^+$ cell culture were listed below:

| Cell factors in the culture and the sources thereof | |
| --- | --- |
| Factors | Sources |
| FL | Immunex |
| Tpo | Glaxo |
| SCF | Sandos |
| IL-6 | Sandos |
| IL-3 | Sandos |
| G-CSF | Amgen |
| GM-CSF | Amgen |

Antibody

Mono-clone antibody used in a flow cytometry included CD34-FITC, HLA-DR-FITC, CD33-PE, CD1a-PE, CD42b-PE, came from Pharmingen Co.

Detection of Effects on Proliferation and Differentiation of CD43+ Hemotapoietic Stem/Ancestor Cells CD43+ hemotapoietic stem/ancestor cells were cultured in a medium consisting of IMDM, 15% FCS, 15% HS, 40 ng/ml FL, 20 ng/ml Tpo, 200 ng/ml SCF, 10 ng/ml IL-6, 10 ng/ml IL-3 and 2×104 u/mlG-CSF. CD34+ cells were incubated and cultured in a 24-cell plate, $3 \times 10^4$ cells/ml, 1 ml/cell. 3 Cells, as a group, were treated with proteoglycan extracts of Spirulina at a dose of 0, 0.2, 0.4 and 0.8 mg/ml, respectively. Cells were cultured at 37° C. under 5% $CO_2$ and a saturated humidity, and added by cell factors every 48 hours. After cultured ten days, cells were harvested, and detected for the cell phenotype with the corresponding fluorentscent antibody.

Experimental Results:

In the presence of FL, TPO, SCF, IL-6, IL-3 and G-CSF, the proliferation of CD34+ cells showed a negative relation to concentrations of Proteoglycan extracts of Spirulina. That is, in the absence of Proteoglycan extracts of Spirulina, cell proliferation and differentiation were active, and cell numbers and differentiation rate were increased. After cultured for 10 days, most CD34+ cells differentiated into mature cells. With the increase of concentrations of Proteoglycan extracts of Spirulina, cell proliferation decreased, and cell deformation and anchoring cells were increased under a microscope. This demonstrated that Proteoglycan extracts of Spirulina could reverse the proliferation of CD34+ cells boosted by cell factors, and could decrease the differentiation rate of CD34+ cells. After the culture, the percentage of CD34+ cells and granular and nucleus ancestor cells in the treated groups were higher than those of the groups only treated by cell factors.

Treated with different concentrations of Proteoglycan extracts of Spirulina, CD34+ cells was detected by a flow cytometry after cultured for 10 days. Results were shown below:

| Proteoglycan extracts of Spirulina concentration (mg/ml) | Cell percentage (%) | | | | |
| --- | --- | --- | --- | --- | --- |
| | CD34+ | CD34+CD33+ | CD34+CD42b+ | CD1a+ | HLA-DR+ |
| 0 | 0.07 | 0.08 | 0 | 1.7 | 26.87 |
| 0.2 | 1.10 | 0.71 | 0.16 | 13.09 | 73.94 |
| 0.4 | 4.83 | 2.08 | 1.77 | 23.12 | 86.49 |
| 0.8 | 25.75 | 7.78 | 9.03 | 19.02 | 80.98 |

From the above table, when the concentration of proteoglycan extracts of Spirulina was increased, the content of CD34+ cells was accordingly increased significantly. So were the content of CD34+CD33+ cells which represent granular and nucleus ancestor cells and that of CD34+CD42b+ cells which represent monocyte ancestor cells. From the above table also, it showed the content of CD1a+ and HLA-DR+ that represent dendritic cells (DC) was significantly increased with the increase of concentrations of proteoglycan extracts of Spirulina. There were a lot of typical dendritic cells emerged in the culture. This indicated that proteoglycan extracts of Spirulina according to the invention had effects on inducing to differentiate CD34+ cells into dendritic cells, reaching a peak at a dose of 0.4 mg/ml of the extracts. Proteoglycan extracts of Spirulina stimulating lymphocyte to secret cell factors The following table showed that Proteoglycan extracts of Spirulina with different dosages stimulated lymphocyte to secret IL-2, IL-3, GM-CSF and IFN-γ. It showed that Proteoglycan extracts of Spirulina had significant effects on stimulating lymphocyte to secret GM-CFS, which were related to the dosage of the extracts used. With the increase of the dosage of proteoglycan extracts of Spirulina used, GM-CSF's secretion was correspondingly increased. When the concentration of proteoglycan extracts of Spirulina was 0.8 mg/ml, GM-CSF secretion amount was 1.15 times as that of the untreated. However, stimulation effects of Proteoglycan extracts of Spirulina on secreting IL-2, IL-3 and IFN-γ were not significant.

Proteoglycan extracts of Spirulina stimulating human peripheral blood lymphocyte secrete cytokine

| Proteoglycan extracts of Spirulina (mg/ml) | 0 | 0.2 | 0.4 | 0.8 |
|---|---|---|---|---|
| GM-CSF (pg/ml) | 20.4 | 67.3 | 196.2 | 235.3 |
| IL-2 (pg/ml) | 0 | 1.2 | 0 | 0 |
| IL-3 (pg/ml) | 3.2 | 3.2 | 2.9 | 3.0 |
| IFN-γ (pg/ml) | 13.8 | 12.5 | 12.8 | 13.0 |

Conclusion:

1. Proteoglycan extracts of Spirulina could negatively regulate proliferation of umbilic $CD34^+$ hemopoietic stem/ancestor cells in the presence of cell factors, and greatly slower the differentiation of $CD34^+$ cells. In the $CD34^+$ cells culture system, with the increase of concentrations of proteoglycan extracts of Spirulina, the content of $CD34^+$ hemopoietic stem/ancestor cells, $CD34^+CD33^+$ myeloid ancestor cells and $CD34^+CD42b^+$ macronucleus ancestor cells was much higher than that in a group to which only cell factors were added. This revealed that proteoglycan extracts of Spirulina could partly inhibit the proliferation of $CD34^+$ by cell fators, slower the differentiation of hemopoietic stem/ancestor cells, make myeloid and macronucleus ancestor cells in a higher proportion, and keep hemopoiesis for a longer time. It was expected that in an animal experiment, the recruit of myelocytes and platelet by proteoglycan extracts of Spirulina would be later than that by cell factors, but the maintenance of myelocytes and platelet by them would be in evidence.

2. Dendritic cell (DC) is the most efficient antigen-presenting cell (APC), which plays an important role in immunoreaction of host. It can recognize the mutant cells, transfer signals to effector cells, and kill tumor cells at least. In vivo, DC is often too few to take functions. So how to increase the number of DC becomes one of the focuses in studying on antitumor immunotherapy and its clinic application. Although no DC induced factors such as GM-CSF, IL-4 or TNF-α are added to the culture system in the present invention, the proportion of $Cd1a^+$ and $HLA-DR^+$ cells (important surface marker of DC) increases along with the increasing of concentrations of proteoglycan extracts of Spirulina. It shows that proteoglycan extracts of Spirulina can induce $CD34^+$ hemopoietic stem/ancestor cells differentiation into DC. When concentrations of proteoglycan extracts of Spirulina are at 0.4 mg/ml, the induced efficiency becomes the highest (the content of $CD1a^+$ and $HLA-DR^+$ cells increased respectively from that of 1.70% and 26.87% to 23.12% and 86.49% in the control group). It implies that proteoglycan extracts of Spirulina are of a potential value and have wide prospects in antitumor immunotherapy.

3. Proteoglycan extracts of Spirulina can remarkably stimulate lymphocyte to secrete GM-CSF, with a typical relationship with the dosage of the extracts. The secretion of GM-CSF increases obviously along with the increasing of concentrations of proteoglycan extracts of Spirulina (the secretion of GM-CSF increasing by 11.5 times with a concentration of 0.8 mg/ml). It reveals that proteoglycan extracts of Spirulina can improve the recovery of haematogenous function, and have wide effects on promoting hemopoietic cells proliferation. In addition, GM-CSF is one of the most important cell factors to promote DC proliferation, maturing and function, which is one of the possible mechanisms of DC formation induced by proteoglycan extracts of Spirulina according to the invention.

We claim:

1. An anticancer composition comprising a therapeutically effective amount of proteoglycan extract from Spirulina with or without a pharmaceutically acceptable carrier, wherein the proteoglycan extract from Spirulina is prepared by the following steps of:
    a) dissolving a dry powdered Spirulina in 5–20 times water by weight and breaking the Spirulina cell walls;
    b) heating a solution obtained from step a) at 60°–100° C., and cooling the heated solution to separate a liquid phase from the solution;
    c) adjusting pH of said liquid phase to 3.8–4.2, and filtering said liquid phase to obtain a filtrate; and
    d) adjusting the filtrate to pH 7, and concentrating the filtrate.

2. The composition according to claim 1, wherein said water in step a) is 8–15 times by weight of said dry powdered Spirulina.

3. The composition according to claim 3, wherein said water in step a) is 10 times by weight of said dry powdered Spirulina.

4. The composition according to claim 1, wherein said step b) is conducted at a temperature of 80° C.–95° C.

5. The composition according to claim 4, wherein step b) is conducted at a temperature of 90° C.

6. A hemogram-improving composition comprising a therapeutically effective amount of proteoglycan extract from Spirulina with or without a pharmaceutically acceptable carrier, wherein the proteoglycan extract from Spirulina is prepared by the following steps of:
    a) dissolving a dry powdered Spirulina in 5–20 times water by weight, and breaking the Spirulina cell walls;
    b) heating a solution obtained from step a) at 60°–100° C., and cooling the heated solution to separate a liquid phase from the solution;
    c) adjusting pH of said liquid phase to 3.8–4.2, and filtering said liquid phase to obtain a filtrate; and
    d) adjusting the filtrate to pH 7, and concentrating the filtrate.

7. The composition according to claim 6, wherein said water in step a) is 8–15 times by weight of said dry powdered Spirulina.

8. The composition according to claim 7, wherein said water in step a) is 10 times by weight of said dry powdered Spirulina.

9. The composition according to claim 6, wherein said step b) is conducted at a temperature of 80° C.–95° C.

10. The composition according to claim 9 wherein said step b) is conducted at a temperature of 90° C.

11. An anti-irradiation composition comprising a therapeutically effective amount of proteoglycan extract from Spirulina with or without a pharmaceutically acceptable carrier, wherein the proteoglycan extract from spirulina is prepared by the following steps of:
    a) dissolving a dry powdered Spirulina in 5–20 times water by weight, and breaking the Spirulina cell walls;
    b) heating a solution obtained from step a) at 60°–100° C., and cooling the heated solution to separate a liquid phase from the solution;
    c) adjusting pH of said liquid phase to 3.8–4.2, and filtering said liquid phase to obtain a filtrate; and
    d) adjusting the filtrate to pH 7, and concentrating the filtrate.

12. The composition according to claim 11, wherein said water in step a) is 8–15 tunes by weight of said dry powdered Spirulina.

13. The composition according to claim 12, wherein said water in step a) is 10 times by weight of said dry powdered Spirulina.

14. The composition according to claim 11, wherein said step b) is conducted at a temperature of 80° C.–95° C.

15. The composition according to claim 14, wherein said step b) is conducted at a temperature of 90° C.

16. A DNA-repairing composition comprising a therapeutically effective amount of proteoglycan extract from Spirulina with or without a pharmaceutically acceptable carrier, wherein the proteoglycan extract from Spirulina is prepared by the following steps of:
   a) dissolving a dry powdered Spirulina in 5–20 times water by weight, and breaking the Spirulina cell walls;
   b) heating a solution obtained from step a) at 60°–100° C., and cooling the heated solution to separate a liquid phase from the solution;
   c) adjusting pH of said liquid phase to 3.8–4.2, and filtering said liquid phase to obtain a filtrate; and
   d) adjusting the filtrate to pH 7, and concentrating the filtrate.

17. The composition according to claim 16, wherein said water in step a) is 8–15 times by weight of said dry powdered Spirulina.

18. The composition according to claim 17, wherein said water in step a) is 10 times by weight of said dry powdered Spirulina.

19. The composition according to claim 16, wherein said step b) is conducted at a temperature of 80° C.–95° C.

20. The composition according to claim 19, wherein said step b) is conducted at a temperature of 90° C.

21. An antivirus composition comprising a therapeutically effective amount of proteoglycan extract from Spirulina with or without a pharmaceutically acceptable carrier, wherein the proteoglycan extract from Spirulina is prepared by the following steps of:
   a) dissolving a dry powdered Spirulina in 5–20 times water by weight, and breaking the Spirulina cell walls;
   b) heating a solution obtained from step a) at 60°–100° C., and cooling the heated solution to separate a liquid phase from the solution;
   c) adjusting pH of said liquid phase to 3.8–4.2, and filtering said liquid phase to obtain a filtrate; and
   d) adjusting the filtrate to pH 7, concentrating, and drying if necessary.

22. The composition according to claim 21, wherein said water in step a) is 8–15 times by weight of said dry powdered Spirulina.

23. The composition according to claim 22, wherein said water in step a) is 10 times by weight of said dry powdered Spirulina.

24. The composition according to claim 21, wherein said step b) is conducted at a temperature of 80° C.–95° C.

25. The composition according to claim 24, wherein said step b) is conducted at a temperature of 90° C.

26. An immunoenhancing composition comprising a therapeutically effective amount of proteoglycan extract from Spirulina with or without a pharmaceutically acceptable carrier, wherein the proteoglycan extract from Spirulina is prepared by the following steps of:
   a) dissolving a dry powdered Spirulina in 5–20 times water by weight; and breaking the Spirulina cell walls;
   b) heating a solution obtained from step a) at 60°–100° C., and cooling the heated solution to separate a liquid phase from the solution;
   c) adjusting pH of said liquid phase to 3.8–4.2, and filtering said liquid phase to obtain a filtrate; and
   d) adjusting the filtrate to pH 7, and concentrating the filtrate.

27. The composition according to claim 26, wherein said water in step a) is 8–15 times by weight of said dry powdered Spirulina.

28. The composition according to claim 27, wherein said water in step a) is 10 times by weight of said dry powdered Spirulina.

29. The composition according to claim 26, wherein said step b) is conducted at a temperature of 80° C.–95° C.

30. The composition according to claim 29, wherein said step b) is conducted at a temperature of 90° C.

31. A dendrite-like-cell-activating composition comprising a therapeutically effective amount of proteoglycan extract from Spirulina with or without a pharmaceutically acceptable carrier, wherein the proteoglycan extract from Spirulina is prepared by the following steps of
   a) dissolving a dry powdered Spirulina in 5–20 times water by weight, and breaking the Spirulina cell walls;
   b) heating a solution obtained from step a) at 60°–100° C., and cooling the heated solution to separate a liquid phase from the solution;
   c) adjusting pH of aid liquid phase to 3.8–4.2, and filtering said liquid phase to obtain a filtrate; and
   d) adjusting the filtrate to pH 7, and concentrating the filtrate.

32. The composition according to claim 31, wherein said water in step a) is 8–15 times by weight of said dry powdered Spirulina.

33. The composition according to claim 32, wherein said water in step a) is 10 times by weight of said dry powdered Spirulina.

34. The composition according to claim 31, wherein said step b) is conducted at a temperature of 80° C.–95° C.

35. The composition according to claim 34, wherein said step b) is conducted at a temperature of 90° C.

36. A process for preparing a proteoglycan extract from Spirulina, including the following steps of:
   a) dissolving a dry powdered Spirulina in 5–20 times water by weight and breaking the Spirulina cell walls;
   b) heating a solution obtained from step a) at 60°–00° C., and cooling the heated solution to separate a liquid phase from the solution;
   c) adjusting pH of said liquid phase to 3.8–4.2, and filtering said liquid phase to obtain a filtrate; and
   d) adjusting the filtrate to pH 7, and concentrating the filtrate.

37. The process according to claim 36, wherein said water in step a) is 8–15 times weight of said dry powdered Spirulina.

38. The process according to claim 37, wherein said water in step a) is 10 times by weight of said dry powdered Spirulina.

39. The process according to claim 36, wherein step b) is conducted at a temperature of 80° C.–95° C.

40. The process according to claim 39, wherein said step b) is conducted at a temperature of 90° C.

41. A composition comprising a proteoglycan extract from Spirulina with or without a pharmaceutically acceptable carrier, wherein the proteoglycan extract from Spirulina is prepared by the following steps of:
   a) dissolving a dry powdered Spirulina in 5–20 times water by weight, and breaking the Spirulina cell walls;

b) heating a solution obtained from step a) at 60°–100° C., and cooling the heated solution to separate a liquid phase from the solution;

c) adjusting pH of said liquid phase to 3.8–4.2, and filtering said liquid phase to obtain a filtrate; and d) adjusting the filtrate to pH 7, and concentrating the filtrate.

42. The composition according to claim 41, wherein said water in step a) is 8–15 times by weight of said dry powdered Spirulina.

43. The composition according to claim 42, wherein said water in step a) is 10 times by weight of said dry powdered Spirulina.

44. The composition according to claim 41, wherein said step b) is conducted at a temperature of 80° C.–95° C.

45. The composition according to claim 44, wherein said step b) is conducted at a temperature of 90° C.

46. The composition according to claim 41, wherein step d) further comprises drying the filtrate.

47. The composition according to claim 1, wherein step d) further comprises drying the filtrate.

48. The composition according to claim 6, wherein step d) further comprises drying the filtrate.

49. The composition according to claim 11, wherein step d) further comprises drying the filtrate.

50. The composition according to claim 16, wherein step d) further comprises drying the filtrate.

51. The composition according to claim 21, wherein step d) further comprises drying the filtrate.

52. The composition according to claim 26, wherein step d) further comprises drying the filtrate.

53. The composition according to claim 31, wherein step d) further comprises drying the filtrate.

54. The process according to claim 36, wherein step d) further comprises drying the filtrate.

* * * * *

UNITED STATES PATENT AND TRADEMARK OFFICE
CERTIFICATE OF CORRECTION

PATENT NO.       : 6,893,642 B1
APPLICATION NO. : 10/031520
DATED            : May 17, 2005
INVENTOR(S)      : Qing Qi et al.

It is certified that error appears in the above-identified patent and that said Letters Patent is hereby corrected as shown below:

Col. 1, line 67, delete "dedrite" and insert therefor --dendrite--.

Col. 3, line 58, delete "spry-dried" and insert therefor --spray-dried--.

Col. 5, line 16, delete "313.3 ± 24054" and insert therefor --313.3 ± 24.54--.

Col. 5, line 62, delete "leucocytes" and insert therefor --leukocytes--.

Col. 6, line 5, delete "that that" and insert therefor --than that--.

Col. 6, line 29, "Expreiment" and insert therefor --Experiment--.

Col. 7, line 37, delete "HI-60" and insert therefor --HL-60--.

Col. 10, line 46, delete "does" and insert therefor --dose--.

Col. 11, line 1, delete "ml/l" and insert therefor --mol/l--.

Col. 13, line 54, delete "IMDM" and insert therefor --1MDM--.

Col. 14, line 53, delete "secret" and insert therefor --secrete--.

Col. 14, line 56, delete "secret" and insert therefor --secrete--.

Col. 15, line 25, delete "fators" and insert therefor --factors--.

Col. 15, line 36, delete "least" and insert therefor --last--.

Col. 15, line 42, delete "Cdla+" and insert therefor --Cd1a$^{+}$--.

Claim 12, col. 16, line 66, delete "tunes" and insert therefor --times--.

Claim 31, col. 18, line 26, delete "aid" and insert therefor --said--.

UNITED STATES PATENT AND TRADEMARK OFFICE
CERTIFICATE OF CORRECTION

PATENT NO. : 6,893,642 B1
APPLICATION NO. : 10/031520
DATED : May 17, 2005
INVENTOR(S) : Qing Qi et al.

It is certified that error appears in the above-identified patent and that said Letters Patent is hereby corrected as shown below:

Claim 36, col. 18, line 44, delete " -00°" and insert therefor -- -100°--.

Signed and Sealed this

Seventeenth Day of April, 2007

JON W. DUDAS
*Director of the United States Patent and Trademark Office*